United States Patent

Manseur et al.

Patent Number: 5,816,245
Date of Patent: Oct. 6, 1998

[54] ELECTRONIC PNEUMOTHORAX MONITORING DEVICE

[76] Inventors: Rachid Manseur, P.O. Box 15632, Pensacola, Fla. 32514; D. Jim Rawlings, 4247 Heath Rd., Jacksonville, Fla. 32207

[21] Appl. No.: 457,052

[22] Filed: Jun. 1, 1995

[51] Int. Cl.$^6$ ..................................................... A61B 5/00
[52] U.S. Cl. ....................... 128/664; 128/665; 128/653.1
[58] Field of Search ........................... 128/633–4, 664–6, 128/630, 653.1; 607/88–91

[56] References Cited

U.S. PATENT DOCUMENTS

| | | | |
|---|---|---|---|
| 4,738,264 | 4/1988 | Orlando | 128/721 |
| 4,909,260 | 3/1990 | Salem et al. | 128/721 |
| 4,974,591 | 12/1990 | Awazu et al. | 128/664 |
| 4,989,612 | 2/1991 | Fore | 128/721 |
| 5,017,019 | 5/1991 | Pompei | 128/664 |
| 5,107,846 | 4/1992 | Atlas | 128/721 |
| 5,267,563 | 12/1993 | Swedlow et al. | 128/664 |
| 5,402,779 | 4/1995 | Chen et al. | 128/664 |

FOREIGN PATENT DOCUMENTS

| 2057886 | 9/1979 | United Kingdom | 607/88 |
|---|---|---|---|

OTHER PUBLICATIONS

Beek et al, "Continuous Pneumothorat Monitoring by Rem. Hance Measurement," *Applied Optics*, vol. 32, No. 4, Feb. 1, 1993, pp. 454–460.

Gomar et al, "An Electronic Device (Episensor) for Detection of the Interpleural Space," *Regional Anestesia*, vol. 1C, No. 2, Mar.–Apr. 1991, pp. 112–115.

*Primary Examiner*—Robert Nasser

[57] ABSTRACT

The device presented here is a device for detecting the presence of pneumothorax in a patient including a non-coherent light source for shining light on a patient, mounted on a first patch, capable of being attached to the patient, a light detector for receiving light from the patient mounted on a second light shielding patch, capable of being attached to the patient, where the detector produces a first signal in response to received light, wherein the first and second patches being independently attachable to the patient and removable from the patient, a driving circuit for causing the light source to turn on and off at a predetermined frequency, a circuit for receiving the first signal from said light detector including a bandpass filter tuned to the predetermined frequency and producing a second signal indicating the presence of pneumothorax when said first signal exceeds a threshol, and an alarm for producing an alarm indicating the presence of pneumothorax in response to said second signal.

1 Claim, 3 Drawing Sheets

ELECTRONIC PNEUMOTHORAX MONITORING DEVICE

INFORMATION DISCLOSURE STATEMENT

Pneumothorax is the collapse of a lung caused by the presence of air in the pleural cavity. This condition can occur accidentally, when the chest wall is perforated and air finds its way from the outside into the pleural cavity or when the lung is perforated and air from the inside of the lung sips into the pleural cavity. In the case of premature babies (neonates), the risk of pneumothorax is accentuated due to the overall fragility of the patients in general, and those attached to an artificial respirator in particular. It is important to keep a close watch for the occurrence of pneumothorax in patients under risk of getting this condition which can be fatal if it is not detected and treated rapidly.

The invention presented here is an electronic device that can detect the occurrence of pneumothorax in neonates by non intrusive electronic means. In neonates, the chest wall is thin enough to be translucent and, when pneumothorax is suspected, the attending physician dims the ambient lights and shines a small and powerful flash light into the chest of the baby. If pneumothorax is not present, the lung fills the pleural space and absorbs the light. If Pneumothorax is present, the lung has collapsed, the pleural cavity is filled with air and light transilluminates the cavity in a visible manner. The pneumothorax monitoring device described here automates this well known procedure.

PRIOR ART

In the most common prior art, pneumothorax is followed by rapid deterioration of vital signs which leads the attending health care professional to suspect and check for pneumothorax. Under suspicion of pneumothorax, the physician shines a strong light into the suspected chest side, under dimmed ambient lights, and visually verifies the occurrence of pneumothorax by transillumination, as explained above, before initiating immediate treatment.

A computer search for previous U.S. patents relating to pneumothorax lead to seven registered patents, six of which, U.S. Pat. Nos. 5,320,110, 5,204,094, 4,950,233, 4,813,941, 4,799,494, and 4,592,741, describe devices for the treatment of pneumothorax and one, U.S. Pat. No. 5,061,188, describes a manikin for training in the diagnosis and treatment of pneumothorax. None were about the present invention which is directed towards the automatic detection and monitoring of pneumothorax.

In the technical and scientific literature, two articles on the prior art were found. The first is an article titled "Continuous pneumothorax monitoring by remittance measurement," by Johan F. Beek, Henricus J. C. M. Sterenborg, and Martin J. C. van Gemert, found in Applied Optics, Volume 32, No 4, 1 Feb. 1993. In this prior art, the authors directly address the detection of pneumothorax in newborns under ventilation. Their device also uses the well known basic principle of light reflection (remittance) in a pleural cavity filled with air, but it requires a laser light with a set of 5 optical fibers as detectors and some involved computer data processing to achieve detection of pneumothorax. Our invention uses a much less expensive, less costly visible light source and the number of light detectors that can be used in conjunction with a single light source can be adjusted from one to many depending on the degree of monitoring desired. No computer data processing is required for our invention. While addressing the same problem as the authors of this prior art article, our approach and our invention is quite significantly simpler and different.

The second article on prior art, found in the technical and scientific literature is titled "An electronic device (episensor) for detection of the pleural space," by C. Gomar, J. De Andres, C. Cabrer, and M. A. Nalda, in Reg. Anesth., March–April 1991 Vol. 16(2), pp. 112–5. The method described in this prior art article requires insertion of a catheter with a pressure sensor in the patient's chest. Our invention is clearly very different and does not relate to the invasive method described in this prior art.

SUMMARY OF THE INVENTION

This invention uses a light source and a light sensor that can be attached to the chest of a neonate patient. The light source is driven by an electronic circuit that powers the light emitting device, possibly a light emitting diode (LED), and controls the light intensity in accordance to a determined pattern. The light detector will register the light reflected from the patient's chest and will provide an electric signal that varies in accordance with the variations of the reflected light. The light sensor signal is then fed to an electronic filter "tuned" to the variations of said light source. Those skilled in the art will know that it is possible to make the electronic filter characteristics match the characteristics of the light source attached to the patient's chest in such a way that the said filter will respond to the electric signal variations originating from said light source while ignoring other light variations that may be produced by ambient or other lights. One possible implementation is to use an electronic oscillator to drive the light source in such a way that said light source is switched on and off at a frequency $f_0$. The above electronic filter will then consist of a narrow bandpass filter tuned on the frequency $f_0$. However, other schemes can be devised. Pneumothorax is detected if a sufficient amount of reflected light, originating from the device light source, is registered by the light sensor. The device will then alert medical personnel for fast treatment of the patient.

As those skilled in the art will know, the electronic circuits required for this invention can be implemented by use of analog electronics or by a combination of analog and digital electronics including programmable devices such as microprocessors or microcontrollers.

As an electronic device, the invention described here can easily be connected to a computer by means well known to those skilled in the art. Therefore, a computer can be programmed to monitor several units installed to detect the occurrence of pneumothorax in one or several patients. Said computer thus connected can easily be programmed to activate various types of alarm systems should a pneumothorax condition appear. Further more said computer can just as easily be programmed to identify the patient and even the chest side that experiences pneumothorax in cases of multiple patients being monitored.

The invention may also be built as a portable hand-held, battery powered unit for routine checks of patients or as a bed unit for the continuous surveillance of a patient.

Those skilled in the art will understand also that modern electronics allows connections between relevant parts of the invention to be implemented by use of electric wires, fiber optics with optical coupling devices, or wireless by use of radio equipment in cases when wires and cables are undesirable.

BRIEF DESCRIPTION OF THE DRAWINGS

The accompanying drawings with the ongoing descriptions will provide a complete understanding of the invention presented here.

DETAILED DESCRIPTION OF THE EMBODIMENT

Figure 1:
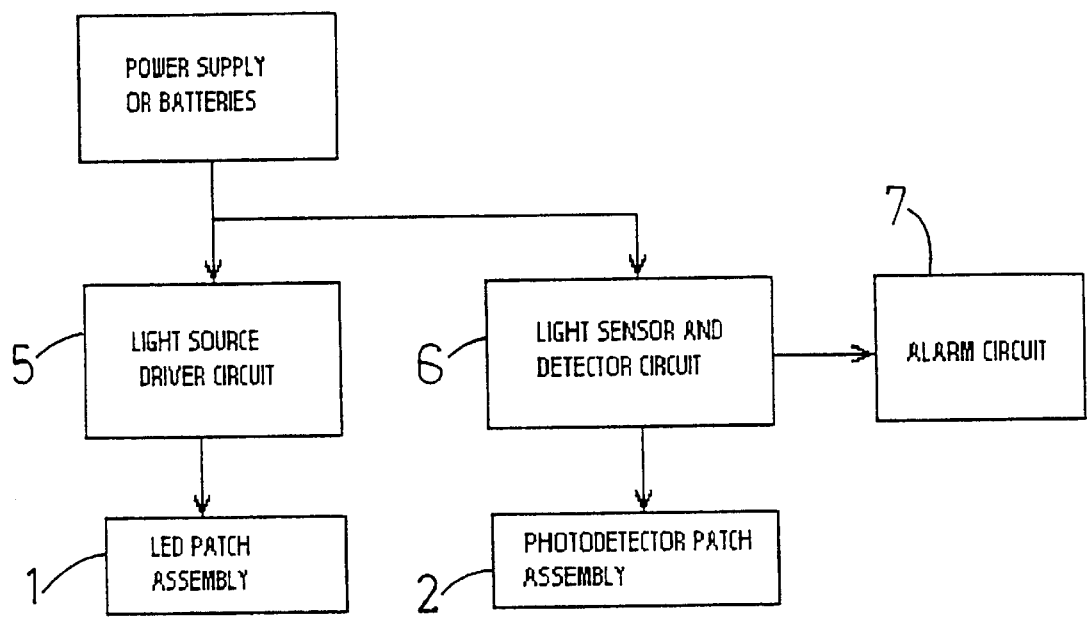
FIG. 1 is a block diagram representation of the invention and shows the major blocks of the pneumothorax detection device.
Figure 2:
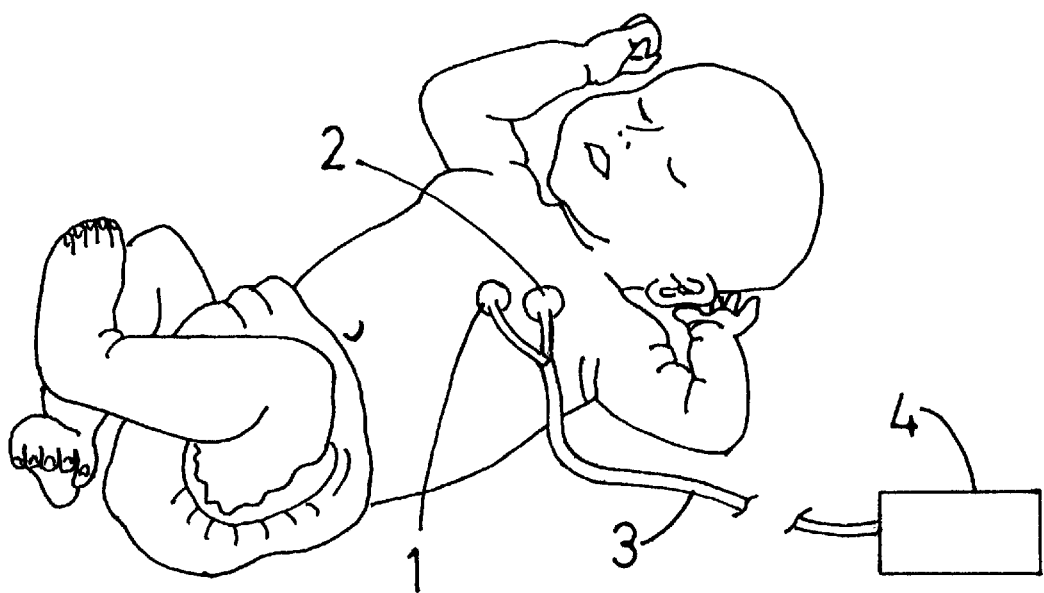
FIG. 2 helps explain the basic principles of operation of the invention and shows how the light source and the light sensor attach to the patient chest.

As illustrated in FIG. 1, this invention consists of a non heating light source 8, possibly a high intensity Light Emitting Diode (LED) mounted on a plastic patch assembly 1 to be attached to the chest of the patient, as described in FIG. 2, in such a way that the light is directed towards the chest. The light source is driven by an electric signal generated by the Light Source Driver Circuit 5. One or more light sensors 9, possibly photoreceptors or photoresistors, mounted on a dark opaque plastic patch assembly 2 are also to be attached to the patient's chest, as illustrated in FIG. 2, to monitor the light reflections from the chest of the patient. FIG. 2 also shows the electric wires 3 connecting said light source and light sensor to the rest of the invention described by box 4. Changes in the light sensor electric signal are monitored by the Light Sensor Detector Circuit 6. This detector circuit may include an active electronic filter to enhance detection of reflected light originating from said light source and reduce the effects of any other light changes that may occur in the room. When the light sensor circuit detects enough reflected light, i.e. the received light exceeds a threshold, to suspect that pneumothorax has occurred, the alarm circuit 7 will be activated to alert medical personnel.

BASIC PRINCIPLE OF OPERATION

Figure 3:
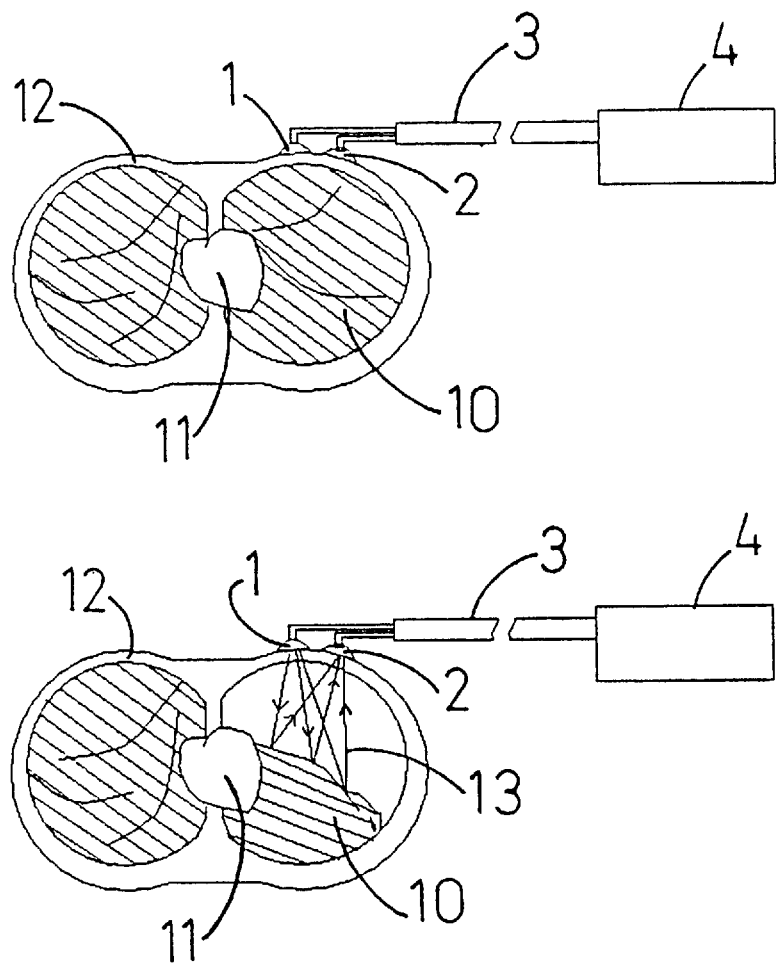
FIG. 3 further details the basic principle of operation of the invention.

FIG. 3 shows a schematic transverse cross section representation of a patient's thorax with one side of the chest under the pneumothorax monitoring device. The heart 11 is shown in dark shading for illustration only. For neonates, the chest wall 12 is thin enough to be translucent and much of the light energy crosses the chest wall into the pleural cavity.

The light source patch assembly 1 is attached to one side of the chest of the patient in such a way as to direct all the light towards the chest. To maximize the intensity of the light incident into the chest of the patient, a reflective coating may be applied to the chest side of the patch used to attach the light source to the patient's chest.

The light sensor patch assembly 2 is also attached to the same chest side of the patient near the light source and in such way as to receive any light originating from the chest. To minimize sensitivity of the invention to ambient light, the light sensor should be protected by dark opaque material, thereby shielding ambient lights.

The top drawing in FIG. 3 shows a healthy lung 10 filling the pleural cavity. The light out of patch assembly 1 gets absorbed by the lung and no light reflection reaches back to the light sensor patch assembly 2. The bottom drawing shows a pneumothorax condition. The lung 10 has collapsed and the pleural cavity is now filled with air. Light from patch assembly 1 gets through the chest wall 12 and scatters into the air-filled cavity. Two rays of light 13 are shown to illustrate light being reflected back to the light sensor under the patch assembly 2 allowing detection of the pneumothorax condition. To avoid false alarms due to ambient light variations, it is necessary to enhance the light sensor's sensitivity to the light emanating from the device light source and to reduce as much as possible, the sensor's sensitivity to all other present interfering light sources. The light sensor circuit must therefore be "tuned" to the light from the device light source.

One possible way to accomplish this tuning is to use a light at a particular wavelength, for example infrared light of a given wavelength and a corresponding sensor, manufactured to sense light having that particular wavelength.

Another way is to use a time varying light source and to design a sensor that can detect whatever particular variations were characteristic of the light source. To illustrate this concept, in our prototype, the LED was driven by an oscillator at a frequency of about 25 Hz. The voltage variations on the sensing photoreceptor were filtered by a narrow bandpass filter, tuned at the same frequency (25 Hz). The frequency was chosen to avoid the ambient light flicker at 60 Hz or 120 Hz and any harmonics thereof.

Those skilled in the art will understand that the particular embodiment of the invention described here is for illustration only and is in no way restrictive. Therefore, several changes and modifications can be made and various equivalents resorted to, without departing from the scope and spirit of the invention as described in the appended claims.

We claim:

1. A device for detecting the presence of pneumothorax in a patient comprising:
   a. a non-coherent light source for shining light on a patient, mounted on a first patch, capable of being attached to the patient;
   b. a light detector for receiving light from the patient mounted on a second light shielding patch, capable of being attached to the patient, said detector producing a first signal in response to received light, wherein the first and second patches being independently attachable to the patient and removable from the patient;
   c. driving means for causing the light source to turn on and off at a predetermined frequency;
   d. means for receiving the first signal from said light detector including a bandpass filter tuned to the predetermined frequency and producing a second signal indicating the presence of pneumothorax when said first signal exceeds a threshold; and
   e. alarm means for producing an alarm indicating the presence of pneumothorax in response to said second signal.

* * * * *